United States Patent [19]

Erekson et al.

[11] Patent Number: 4,826,796
[45] Date of Patent: May 2, 1989

[54] MIXED BASIC METAL OXIDE CATALYST FOR OXIDATIVE COUPLING OF METHANE

[75] Inventors: Erek J. Erekson, LaGrange; Anthony L. Lee, Glen Ellyn, both of Ill.

[73] Assignee: Institute of Gas Technology, Chicago, Ill.

[21] Appl. No.: 172,808

[22] Filed: Mar. 28, 1988

[51] Int. Cl.$^4$ .................. B01J 21/02; B01J 23/02; B01J 23/04; B01J 23/10
[52] U.S. Cl. ..................... 502/202; 502/243; 502/303; 502/341; 502/342; 502/344
[58] Field of Search ............... 502/203, 303, 341, 342, 502/344, 243; 585/400, 500

[56] References Cited

U.S. PATENT DOCUMENTS

| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,450,310 | 5/1984 | Fox et al. | 502/341 X |
| 4,499,322 | 2/1985 | Jones et al. | 585/500 |
| 4,499,323 | 2/1985 | Gaffney | 585/500 |
| 4,499,324 | 2/1985 | Gaffney | 585/500 |
| 4,523,049 | 6/1985 | Jones et al. | 585/500 |

FOREIGN PATENT DOCUMENTS 254423 1/1988 European Pat. Off. ............ 502/202
86/07351 12/1986 World Int. Prop. O. .......... 585/500

OTHER PUBLICATIONS

Keller, G. E. and M. M. Bhasin, J. of Catalysis 73, 9–19 (1982).
Hinsen, W. and M. Baerns, Chem.-Ztg., 107, 223–226 (1983).
Hinsen, W., W. Bytyn and M. Baerns, Proc. 8th Int. Congr. Catal., Berlin, III 581–592 (1984).
Kimble, James B. and John H. Kolts, "Oxidative Coupling of Methane to Higher Hydrocarbons", Energy Progress, vol. 6, p. 227 (1986).
Driscoll, D. J., W. M. Martir, J. Wang and J. H. Lunsford, J. Am. Chem. Soc. 107, 58–63 (1985).
Ito, T., J. Wang, C. Lin and J. H. Lunsford, J. Am. Chem. Soc. 107, 5062–5064 (1985).
Illingworth, G. F. and G. W. Lester, ACS Petroleum Division Preprints, 12, No. 3, 161 (1967).
Lee, K. W., M. J. Choi, S. B. Kim and C. S. Choi, Ind. Eng. Chem. Res. 26, 1951 (1987).
Kegeyan, E. M., I. S. Vardanyan and A. B. Nalbandyan, Kinetics and Catalysis 17, No. 4, 749–754 and No. 4, 755–759 (1976).

Primary Examiner—W. J. Shine
Attorney, Agent, or Firm—Thomas W. Speckman

[57] ABSTRACT

A catalyst and a process for oxidative coupling of methane, the catalyst being a mixed basic metal oxide catalyst. One preferred catalyst is boron/alkali metal promoted metal oxide.

12 Claims, No Drawings

MIXED BASIC METAL OXIDE CATALYST FOR OXIDATIVE COUPLING OF METHANE

BACKGROUND OF THE INVENTION

1. Field of the Invention

This invention relates to mixed basic metal oxide catalysts for production of higher hydrocarbons by oxidative coupling of methane. Reaction of methane with oxygen in the presence of a mixed basic metal oxide catalyst of this invention results in high conversion of methane with selectivity for ethane and ethylene products. Boron/lithium promoted magnesia catalysts have been found particularly suited for ethane and ethylene production by oxidative coupling at a high production rate.

2. Description of the Prior Art

Methane is currently available in large quantities from natural gas, anaerobic digestion of organic material, and chemical processing sources. However, use of methane as a chemical feedstock has been limited due to its high stability. It has been highly desirable to develop a catalyst for such reactions to enable operation under milder conditions with greater control over thermodynamic and kinetic processes as well as provide product selectivity and high reaction rate.

Oxidative coupling of methane to form higher hydrocarbons has been shown to be effected over a number of metal oxides, but yields of desired products have been low, as discussed by Keller, G. E. and M. M. Bhasin, J. of Catalysis 73, 9–19 (1982). Sodium and lead on alumina has been found to catalyze the formation of ethane and ethylene from methane, as disclosed in Hinsen, W. and M. Baerns, Chem.-Ztg., 107, 223–226 (1983) and Hinsen, W., W. Bytyn and M. Baerns, Proc. 8th Int. Congr. Catal., Berlin, III 581–592 (1984). Several U.S. patents teach a series of supported metal oxides which while effective for the conversion of methane to ethane and ethylene, are based on reducible metal oxides and used in a stoichiometric fashion by alternately exposing them to an oxidizing atmosphere and then to methane in the absence of oxygen. U.S. Pat. Nos. 4,443,644; 4,443,645; 4,443,646; 4,443,647; 4,443,648; 4,443,649; 4,444,984, 4,499,322; 4,499,323; and 4,499,324.

Later work has demonstrated that magnesium oxide and calcium oxide, when promoted with alkali metal salts, are active for oxidative coupling of methane to ethane and ethylene in the presence of oxygen. See Kimble, James B. and John H. Kolts, "Oxidative Coupling of Methane to Higher Hydrocarbons", Energy Progress, Vol. 6, p. 227 (1986); Driscoll, D. J., W. M. Martir, J. Wang and J. H. Lunsford, J. Am. Chem. Soc. 107, 58–63 (1985); and Ito, T., J. Wang, C. Lin and J. H. Lunsford, J. Am. Chem. Soc. 107, 5062–64 (1985). These later catalysts have the advantage of operating continuously, not requiring regeneration or pretreatment.

Borates and boron compounds have been used in partial oxidation of hydrocarbons, such as boric acid to oxidize long chain normal paraffins in the liquid phase (Illingworth, G. F. and G. W. Lester, ACS Petroleum Division Preprints, 12, No.-3, 161 (1967)) and oxidation of n-dodecane in the liquid phase to the corresponding alcohol (Lee, K. W., M. J. Choi, S. B. Kim and C. S. Choi, Ind. Eng. Chem. Res. 26, 1951 (1987)). Boric acid has been used by coating reactor walls in the combustion of methane to eliminate free radical destruction at temperatures of less than 513° C. (Kegeyan, E. M., I. S. Vardanyan and A. B. Nalbandyan, Kinetics and Catalysis 17, No. 4,749–754 and No. 4,755–759 (1976))

SUMMARY OF THE INVENTION

This invention provides a suitable catalyst for and a catalytic process for oxidative coupling of methane to produce higher molecular weight hydrocarbons. The reaction of methane with oxygen is conducted in the presence of a mixed basic metal oxide catalyst at elevated temperature to result in high conversion of methane with high selectivity for ethane and ethylene products. The mixed basic metal oxide catalyst of this invention has the formula:

$$xA \cdot yB \cdot zC \cdot qO$$

wherein

A is an alkali metal selected from lithium, sodium, potassium, rubidium and cesium;

B is a cation which has an ionization state 1 greater than the ionization state of C; B is selected from Group IIIA and IIIB of the Periodic Table, preferably boron, aluminum, yttrium, and lanthanum when C is selected from Group IIA and IIB of the Periodic Table, preferably magnesium, calcium, barium and zinc, and B is selected from Group IVA and IVB of the Periodic Table, preferably silicon, titanium, zirconium, and hafnium when C is selected from Group IIIA and IIIB of the Period Table, preferably boron, aluminum, yttrium, and lanthanum;

x and y are in the mole fractions of z such that when $z=1$ then $x=0.001$ to 0.25, preferably 0.05 to 0.15 and $y=0.01$ to 0.25, preferably 0.03 to 0.10; and q is a number necessary to maintain charge balance with O being oxygen.

In a preferred embodiment, a boron/alkali metal promoted metal oxide catalyst having boron in amounts of about 0.2 to about 20 mole percent (about 0.05 to about 5.0 weight percent), alkali metal promoter selected from the group consisting of lithium, sodium and potassium in amounts of about 0.1 to about 40 mole percent (about 0.1 to about 10 weight percent), metal oxide selected from the group consisting of magnesium oxide, calcium oxide, zinc oxide, and barium oxide are suitable for the catalytic oxidative coupling of methane according to this invention.

DESCRIPTION OF PREFERRED EMBODIMENTS

The process of this invention provides gas phase oxidative coupling of methane by reaction of methane and oxygen in the presence of a mixed basic metal oxide catalyst, such as a boron/alkali metal promoted metal oxide catalyst. Feedstock gas comprising methane suitable for use in the process of this invention may comprise any methane containing gas which does not contain interfering compounds. Preferably, the methane containing gas used in the process of this invention comprises about 25 mole percent up to about 100 mole percent methane. Suitable sources of methane containing gas include natural gas, synthetic natural gas (SNG), product gas from gasification of carbonaceous materials, such as gasification of coal, peat, shale, and the like, as well as products of anaerobic digestion of various biomass materials. These gases principally comprise methane and may contain other hydrocarbon gases such as ethane and propane which may produce corresponding chemical reactions to those of methane in the process of this invention. Purification of such mixed gases comprising principally methane is not usually necessary. These sources of methane containing gas and processes for producing methane are well known in the art. Any oxygen containing gas not containing interfering chemical compounds are useful as a feedstock in this invention. The term "oxygen containing gas" as used throughout this disclosure and claims, refers to gas containing oxygen, such as air or steam, and gases having an oxygen content of up to 100 percent. It is preferred to use oxygen containing gas comprising over 50 volume percent oxygen. The mole percentage of oxygen relative to the mole percentage of methane in the gas mixture subjected to the process of this invention is about 2 to about 40 and preferably about 5 to about 20 mole percent oxygen.

The catalyst of this invention and the catalyst used in the catalytic process for oxidative coupling of methane according to this invention is a mixed basic metal oxide catalyst having the formula $xA.yB.zC.qO$ wherein A, B, C, x, y, z and q have the meanings set forth above with O being oxygen. In a particularly preferred embodiment, the catalyst of this invention is a boron/alkali metal promoted metal oxide catalyst having boron in amounts of about 0.2 to about 20 mole percent (about 0.05 to about 5 weight percent) and preferably about 0.4 to about 2 mole percent (about 0.1 to about 0.5 weight percent); alkali metal promoter selected from the group consisting of lithium, sodium and potassium in amounts of about 0.1 to about 40 mole percent (about 0.1 to about 10 weight percent) and preferably about 0.5 to about 8 mole percent (about 0.5 to about 2.0 weight percent) and the remainder metal oxide selected from the group consisting of magnesium oxide, calcium oxide, zinc oxide, and barium oxide. A preferred catalyst is boron/lithium promoted magnesium oxide having about 0.20 to about 0.30 weight percent boron and about 0.8 to about 1.2 weight percent lithium.

The catalyst of this invention may be prepared by mixing water soluble ions and/or compounds of elements set forth as alkali metal (A) and cation (B) to obtain complete solution of the solids. A wide variety of non-interfering ions may be used to form suitable water soluble compounds as long as they do not cause undesired chemical interference. Suitable such compounds include acids, oxides, hydrides, and nitrates, carbonates, hydroxides, respectively. The aqueous solution of (A) and (B) are added to metal oxide (C) powder and well mixed followed by drying at a sufficient temperature and for a sufficient time to expel volatile components. The mixture is then crushed and sieved to a small size for catalytic use. Conventional and well known catalyst manufacturing techniques may be employed to produce the catalyst material noted above. When preparing these catalytic materials, it is preferred to employ manufacturing techniques resulting in a product having a substantially uniform or homogeneous composition. Shaping of the material may be effected according to conventional techniques of the art, particularly tableting, or pelleting or extrusion. The catalyst may be used unsupported or alternatively it may be supported on an inert support as known to the art, such as alumina, silica, activated carbon and the like.

In preferred embodiments, the catalyst may be prepared by mixing a water soluble compound of boron, such as boric acid, boron oxides, borohydrides, and a water soluble salt of the alkali metal promoter, such as nitrate, carbonate, hydroxide or water soluble ion to obtain complete solution of the solids. The aqueous solution of boron and alkali metal is added to the metal oxide powder with stirring to obtain a homogeneous mixture which may then be dried at a temperature in excess of about 110° C. The dried mixture may then be calcined at a temperature of 700° to 750° C. for a sufficient time to expel volatile portions. The mixture is then crushed and sieved to an appropriately small mesh size of about −6 to about +40, preferably about −12 to about +20 for use as a catalyst.

The catalyst may be placed into a reactor, such as a tubular fixed bed, fluidized bed, moving bed, or other reactor type known to the art. The reaction of methane and oxygen according to this invention is carried out by passing a gaseous mixture comprising methane and oxygen over the mixed basic metal oxide catalyst as defined above at about 500° to about 1100° C., preferably about 600° to about 900° C. Suitable gas residence times are about 0.002 to about 0.00002 hour preferably about 0.0005 to about 0.0001 hour. The reaction may be carried out at about pressures of about 0 to about 1500 psig, preferably about 0 to about 150 psig. Suitable reactor vessels for use at the above operating temperatures and pressures are well known to the art.

The specific examples are intended to be illustrative only and are not intended to limit the invention in any way.

EXAMPLE I

A mixture of 3.07 grams Fisher Certified lithium nitrate and 0.43 gram Aesar 99.99 percent pure boric acid was added to a beaker. Deionized water, 50 ml, was added to the beaker and stirred to obtain complete solution of the solids in the water. The aqueous solution of lithium nitrate and boric acid was slowly added to 30.0 grams alpha magnesium oxide powder and stirred to obtain a homogeneous preparation which was then dried overnight at 118° C. The composition of the mixture was 1.0 weight percent elemental lithium and 0.24 weight percent elemental boron. The mixture was then calcined for 15 minutes at 700° C. and crushed and sieved to −12+20 mesh. Chemical analysis after calcining showed 0.97 weight percent elemental lithium and 0.17 weight percent elemental boron. Surface area of the product was 2.0 meters$^2$/gram. The product was then used as a catalyst in accordance with Example X following which analysis showed 0.94 weight percent lithium, 0.20 weight percent boron, and surface area of 1.5 meters$^2$/gram.

EXAMPLES II–XII

For comparison lithium promoted magnesium oxide catalyst with 1.0 weight percent lithium (Example II) and boron promoted magnesium oxide catalyst with 0.24 weight percent boron (Example III) were prepared in a manner similar to Example I. Boron/lithium promoted magnesium oxide catalyst according to this invention was prepared having 1.0 weight percent lithium and 0.18 weight percent boron (Example IV). The promoter amounts are expressed in weight percent of the elemental lithium and boron mixed in preparation of the catalyst unless otherwise noted. Twelve grams of −12+20 mesh of the denoted catalyst powder was supported on quartz wool in a one inch O.D. quartz tube reactor. A mixture of air and methane in mole percentages indicated were fed to the reactor maintained at the indicated temperatures and passed over the indicated catalyst where oxidative coupling of methane took place at atmospheric pressure and Weight Hourly Space Velocity (WHSV) of 5000 cm$^3$/g cat.-hr. The product gas was analyzed and conversion expressed as the percent of methane molecules that react; selectivity expressed as percentage of reacting methane molecules forming ethane or ethylene; and rate of ethane and ethylene formation expressed as standard cubic centimeters per gram of catalyst per hour. Results are shown in Table 1:

TABLE 1

| Example | Promoter Weight % | | Feed - Mole % | | Temp. °C. | Conversion % | Selectivity % | Rate scc/gcat-hr. |
|---|---|---|---|---|---|---|---|---|
| | Li | B | Methane | Air | | | | |
| II | 1.0 | — | 87 | 13 | 702 | 4.0 | 80 | 53 |
| III | — | 0.24 | 87 | 13 | 710 | 2.3 | 18 | 8 |
| IV | 1.0 | 0.18* | 87 | 13 | 700 | 4.4 | 88 | 77 |
| V | 1.0 | 1.09* | 85 | 15 | 820 | 3 | 100 | 50 |
| VI | 1.0 | — | 60 | 40 | 784 | 16.7 | 74 | 131 |
| VII | — | 0.24 | 60 | 40 | 781 | 14.1 | 38 | 69 |
| VIII | 1.0 | 0.12 | 60 | 40 | 799 | 16.9 | 75 | 156 |
| IX | 1.0 | 0.20 | 60 | 40 | 796 | 21.2 | 86 | 247 |
| X | 0.97 | 0.17* | 60 | 40 | 801 | 21.7 | 81 | 246 |
| XI | 1.0 | 0.51 | 60 | 40 | 801 | 17.4 | 73 | 159 |
| XII | 2.3 | 0.58 | 50 | 50 | 815 | 17.0 | 73 | 204 |

*Denotes composition after calcining.

It is seen from Table 1 that the boron/lithium promoted magnesium oxide catalyst according to this invention provides greater conversion, selectivity for ethane or ethylene, and greater rate of ethane and ethylene formation per gram of catalyst than either promoter alone.

EXAMPLE XIII

In a manner similar to Example I an aluminum/lithium promoted magnesium oxide catalyst was formed by adding 3.08 grams of Fisher Certified lithium nitrate and 2.63 grams of Fisher Certified aluminum nitrate to a beaker. Deionized water, 50 ml, was added to the beaker and stirred to obtain complete solution of the solids in the water. The aqueous solution of lithium nitrate and aluminum nitrate was slowly added to 30.0 grams of alpha magnesium oxide powder and stirred to obtain a homogeneous preparation which was then dried overnight at 118° C. The composition of the mixture was 1.0 weight percent elemental lithium and 0.6 weight percent elemental aluminum. The mixture was then calcined for 15 minutes at 700° C. and crushed and seived to −12+20 mesh.

EXAMPLE XIV

The catalyst produced in accordance with Example XIII was used in the same manner as described in Examples II–XII and the results are shown in Table 2:

TABLE 2

| Promoter Weight % | | Feed - Mole % | | Temp. °C. | Conversion % | Selectivity % | Rate scc/gcat-hr. |
|---|---|---|---|---|---|---|---|
| Li | Al | Methane | Air | | | | |
| 1.0 | 0.6 | 60 | 40 | 802 | 17.3 | 45 | 63 |

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A mixed basic metal oxide catalyst having the formula:

$$xA.yB.zC.qO$$

wherein
A is an alkali metal selected from lithium, sodium, potassium, rubidium and cersium;
B is a cation which has an ionization state 1 greater than the ionization state of C;
B is selected from the group consisting of boron, aluminum, yttrium, and lanthanum and C is selected from the group consisting of magnesium, calcium, barium and zinc;
x and y are in mole fractions of z such that when z=1 then x=0.001 to 0.25, and y=0.01 to 0.25; and
q is a number necessary to maintain charge balance with O being oxygen.

2. A catalyst according to claim 1 wherein x=0.05 to 0.15 and y=0.03 to 0.10.

3. A catalyst according to claim 1 wherein A is lithium, B is aluminum and C is magnesium.

4. A mixed basic metal oxide catalyst having the formula:

$$xA.yB.zC.qO$$

wherein
A is an alkali metal selected from lithium, sodium, potassium, rubidium and cesium;
B is a cation which has an ionization state 1 greater than the ionization state of C;
B is selected from the group consisting of silicon, titanium, zirconium and hafnium and C is selected from the group consisting of boron, aluminum, yttrium, and lanthanum;
x and y are in mole fractions of z such that when z=1 then x=0.001 to 0.25, and y=0.01 to 0.25; and
q is a number necessary to maintain charge balance with O being oxygen.

5. A catalyst according to claim 4 wherein x=0.05 to 0.15 and y=0.03 to 0.10.

6. A mixed boron/alkali metal promoted metal oxide catalyst having the formula:

$xA.yB.zC.qO$ wherein
- A is an alkali metal selected from lithium, sodium, and potassium, and present in about 0.1 to about 40 mole percent;
- B is boron which has an ionization state 1 greater than the ionization state of C and is present in about 0.2 to about 20 mole percent;
- C is selected from the group consisting of magnesium, calcium, zinc, and barium present in an amount representing the balance mole percent required; and
- q is a number necessary to maintain charge balance with O being oxygen.

7. A catalyst according to claim 6 wherein said boron is present in about 0.4 to about 2 mole percent.

8. A catalyst according to claim 6 wherein said alkali metal is present in about 0.5 to about 8 mole percent.

9. A catalyst according to claim 6 wherein said alkali metal is lithium.

10. A catalyst according to claim 6 wherein said metal oxide is magnesium oxide.

11. A catalyst according to claim 6 wherein said alkali metal is lithium and said metal oxide is magnesium oxide.

12. A catalyst according to claim 11 wherein said boron is present in about 0.4 to about 2 mole percent and said alkali metal is present in about 0.5 to about 8 mole percent.

* * * * *